United States Patent
Igi et al.

(10) Patent No.: US 7,256,305 B2
(45) Date of Patent: Aug. 14, 2007

(54) PROCESS FOR PRODUCING β-HYDROXYESTER

(75) Inventors: Kimitaka Igi, Osaka (JP); Yoshiro Furukawa, Osaka (JP); Keishi Takenaka, Osaka (JP)

(73) Assignee: Daiso Co., Ltd., Osaka-fu (JP)

(*) Notice: Subject to any disclaimer, the term of this patent is extended or adjusted under 35 U.S.C. 154(b) by 22 days.

(21) Appl. No.: 10/554,104

(22) PCT Filed: Feb. 20, 2004

(86) PCT No.: PCT/JP2004/001986

§ 371 (c)(1),
(2), (4) Date: Oct. 21, 2005

(87) PCT Pub. No.: WO2004/094361

PCT Pub. Date: Nov. 4, 2004

(65) Prior Publication Data

US 2006/0122419 A1 Jun. 8, 2006

(30) Foreign Application Priority Data

Apr. 21, 2003 (JP) .............................. 2003-116239

(51) Int. Cl.
  *C07C 67/36* (2006.01)
  *C07C 67/37* (2006.01)
(52) U.S. Cl. ..................................... 560/114
(58) Field of Classification Search ..................... None
  See application file for complete search history.

(56) References Cited

U.S. PATENT DOCUMENTS

| 6,348,611 B1 | 2/2002 | Lee et al. |
| 2002/0099245 A1 | 7/2002 | Lee et al. |

FOREIGN PATENT DOCUMENTS

| EP | 577206 | 1/1994 |
| EP | 1034842 | 9/2000 |
| JP | 57-183749 | 11/1982 |
| JP | 5-17402 | 1/1993 |
| WO | 02/12161 | 2/2002 |

OTHER PUBLICATIONS

Allmendinger et al. PMSE Preprints 2002, 86, 332-333. (CAS abstract of document number: 136:386507 is used in the office action).*
K. Hinterding et al., "Regioselective Carbomethoxylation of Chiral Epoxides: A New Route to Enantiomerically Pure β-Hydroxy Esters", Journal of Organic Chemistry, vol. 64, No. 7, pp. 2164-2165, 1999.
Journal of the Nippon Kagakukai, vol. 5, pp. 635-640, (1979).
Dalcanale, Enrico et al., "A New Synthesis of 2-(6-Methoxycarbonylhexyl)-cyclopent-2-en-1-one", Synthesis, pp. 492-494, (1986).

* cited by examiner

*Primary Examiner*—James O. Wilson
*Assistant Examiner*—Yevgeny Valenrod
(74) *Attorney, Agent, or Firm*—Wenderoth, Lind & Ponack, L.L.P.

(57) ABSTRACT

A process for producing a β-hydroxyester by reacting an epoxide, an alcohol and carbon monoxide in the presence of a cobalt carbonyl compound as catalyst,
which is characterized in using as co-catalyst, a pyridine derivative having an amino substituent of formula (1),

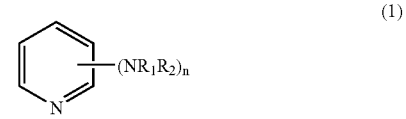

(1)

wherein $R_1$ and $R_2$ are independently hydrogen, formyl, acyl, alkoxycarbonyl, substituted or unsubstituted alkyl, substituted or unsubstituted aralkyl, substituted or unsubstituted aryl, or $R_1$ and $R_2$ may be taken together with the adjacent nitrogen atom to form a ring, and n is an integer of 1 or 2.

13 Claims, No Drawings

PROCESS FOR PRODUCING β-HYDROXYESTER

TECHNICAL FIELD

The present invention relates to a process for preparation of a β-hydroxyester which is useful as an intermediate of an optically active medicine.

BACKGROUND ART

It is reported in many articles that a β-hydroxyester is prepared by reacting an epoxide with carbon monoxide and an alcohol such as methanol, etc. in the presence of a cobalt carbonyl compound such as dicobaltoctacarbonyl complex, etc. (this reaction is called "hydroesterification" hereinafter.), but this reaction lacks in selectivity, is poor in yield and requires high pressure (140 atm) (see for example, Journal of the Nippon Kagakukai, Vol. 5, p 635 (1979)).

Furthermore, it is described in European Patent Publication A 577206 that in order to make this reaction effectively proceed, hydroxypyridines are used as co-catalyst. It is described in US Patent Publication A 2002/0099245 that imidazole, pyrimidine, pyrazine, pyrrole and so on are effective as co-catalyst in this reaction. It is also reported that when an inorganic base is used as co-catalyst, the reaction proceeds at lesser carbon monoxide pressure, different from in the co-catalyst mentioned above (see Synthesis, p 492, 1986 and Japanese Patent Publication A 57-183749).

DISCLOSURE OF INVENTION

However, as above hydroxypyridines are expensive, it is economically disadvantageous to use them in an industrially large scale and the known methods require severe conditions such as using carbon monoxide at higher pressure, etc. On the other hand, in the reaction system using imidazole, pyrimidine, pyrazine, pyrrole and so on as co-catalyst, the reaction is improved in cost, but the reaction condition is severe as in the case of hydroxypyridines, and in order to make the reaction effectively proceed, it is necessary to use a large amount of the co-catalyst to cobalt metal. On the other hand, when using an inorganic base as co-catalyst, the pressure of carbon monoxide is lower and the reaction condition is comparatively mild, but there is such a problem that the reaction term is longer. As such it is a present status that it is impossible to make the reaction effectively proceed under the mild condition by known methods.

The present inventors studied extensively in order to solve above problems, and found that in case of preparation of a β-hydroxyester by hydroesterification, by using a pyridine derivative having an amino substituent group as co-catalyst, in a comparatively small amount thereof, the reaction proceeds in mild condition, while keeping the selectivity of the reaction, the yield and the optical purity in high degree. Thus the present invention was completed.

BEST MODE FOR CARRYING OUT THE INVENTION

Namely the present invention relates to a process for preparation of a β-hydroxyester by reacting an epoxide, an alcohol and carbon monoxide in the presence of a cobalt carbonyl compound as catalyst, which is characterized in using as co-catalyst, a pyridine derivative having an amino substituent group represented by the following formula (1),

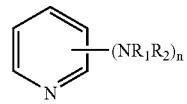

(1)

wherein $R_1$ and $R_2$ are independently hydrogen atom, formyl group, acyl group, alkoxycarbonyl group, substituted or unsubstituted alkyl group, substituted or unsubstituted aralkyl group, substituted or unsubstituted aryl group, or $R_1$ and $R_2$ may be taken together with the adjacent nitrogen atom to form a ring, and n is an integer of 1 or 2, and the pyridine ring in the formula (1) may have other substituent(s) or be fused at positions 2 and 3 or at positions 3 and 4 with a benzene ring to form a fused ring.

The epoxide, a substrate which is used in this reaction is not limited as far as it has an oxylane ring in its molecule, but preferable one is an 1,2-epoxide from the viewpoint of effectively proceeding the reaction.

Preferable examples of the epoxide include an epoxide substituted by alkyl group or aralkyl group such as ethylene oxide, propylene oxide, 1,2-epoxyhexane, 2,3-epoxypropylbenzene, etc., a glycidyl ether such as ethylglycidyl ether, benzylglycidyl ether, etc. or an epihalohydrin such as epichlorohydrin, etc.

The co-catalyst used in the present invention is a pyridine derivative having an amino substituent group(s) represented by the formula (1). The substituent group(s) may be single or plural, preferably single, and the position of it is preferably position 4. Furthermore, other substituent(s) than the essential amino substituent group may be substituted on the pyridine ring as far as they do not affect hydroesterification. Furthermore, the pyridine ring may be fused with a benzene ring to form a quinoline ring or an isoquinoline ring.

When $R_1$ and/or $R_2$ in the formula (1) are substituted or unsubstituted alkyl group, or substituted or unsubstituted aralkyl (arylalkyl) group, alkyl moiety in said groups has preferably 1 to 20 carbon atoms, more preferably 1 to 10 carbon atoms. Alkyl moiety of alkoxycarbonyl group in $R_1$ and/or $R_2$ has preferably 1 to 5 carbon atoms. The total atomic weight of the amino substituent group is preferably 500 or less.

When $R_1$ and $R_2$ are taken together with the adjacent nitrogen atom to form a ring, the said ring is preferably a 4 to 10 membered ring, more preferably a 5 or 6 membered ring. In this case, the total atomic weight of the cyclic amino substituent group is preferably 700 or less.

The pyridine derivative (1) used herein means any compound in which pyridine nucleus, namely a 6 membered heteroaromatic ring containing an imino type nitrogen, constitutes a main part in the said derivative. Even if it is a bicyclic heteroaromatic compound such as quinoline or isoquinoline, such a compound is included in the pyridine derivative, as far as said amino substituent group on pyridine nucleus exists.

The preferable pyridine derivative having an amino substituent group is represented by the following formula (1a):

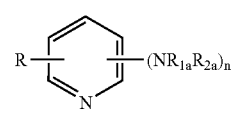

(1a)

wherein R is hydrogen atom or C1 to 6 alkyl group, $R_{1a}$ and $R_{2a}$ are independently, hydrogen atom, C1 to 10 alkyl group, or benzyl group, or $R_{1a}$ and $R_{2a}$ may be taken together with the adjacent nitrogen atom to form a 5 to 6 membered ring, and n is an integer of 1 or 2.

There are exemplified 2-aminopyridine, 3-aminopyridine, 4-aminopyridine, 3,4-diaminopyridine, 2-amino-4-methylpyridine, 4-(methylamino)pyridine, 4-dimethylaminopyridine, 4-pyrrolidinopyridine, 4-piperidinopyridine, 4-(1-piperazinyl)pyridine, 2-(benzylamino)pyridine, and 2-anilinopyridine. Among them a derivative having an amino substituent group at position 4 of the pyridine ring is preferable, and 4-aminopyridine is especially preferable.

In addition, said pyridine derivative may be fit via chemical bond with an insoluble carrier such as a polymer or silica gel. The binding position is not limited and it may bind directly to the pyridine ring or may bind to at least one of $R_1$ and $R_2$ or $R_{1a}$ and $R_{2a}$ of the amino substitution group.

The amount of the pyridine derivative having an amino substituent group is preferably 0.1 to 10 mole equivalents to cobalt metal, more preferably 0.3 to 1 mole equivalent.

A cobalt carbonyl compound used as catalyst in the present reaction is one usually used in known hydroesterification, such as, dicobaltoctacarbonyl, tetracobaltdodecacarbonyl, sodium cobalt tetracarbonyl, cobalt hydrocarbonyl, or hexacarbonylbis(tri-n-butylphosphine)dicobalt.

The cobalt carbonyl compound may be dicobaltoctacarbonyl complex. The dicobaltoctacarbonyl complex is preferably purified one (for example, crystalline complex), and a product containing dicobaltoctacarbonyl complex prepared by known method, for example a solution containing dicobaltcarbonyl complex prepared by reacting carbon monoxide with cobalt acetate or cobalt hydroxide and carbonylating it can be used without purification.

The amount of the cobalt carbonyl compound may be 0.005~0.2 molar equivalent to an epoxide, preferably 0.01-0.1 molar equivalent.

The alcohol used herein is not limited, but preferably is a primary or secondary alcohol having 10 carbon atoms or less. The carbon chain of the alcohol may be branched, straight or cyclic such as methanol, ethanol, n-propanol, n-butanol, isopropanol, cyclohexanol, phenethyl alcohol, or benzyl alcohol, especially preferably, an aliphatic alcohol having 6 carbon atoms or less represented by methanol and ethanol.

The reactant, an alcohol is also served as a solvent, and therefore, a solvent is in principle unnecessary. However, in order to control the viscosity of the reaction medium or for other object, various solvents are used if necessary, preferably such as an ether-solvent, e.g., tetrahydrofuran (THF), diethyl ether, 1,2-diethoxyethane, an ester-solvent, e.g., ethyl acetate, butyl acetate, an aromatic hydrocarbon-solvent, e.g., benzene, toluene, a hydrocarbon-solvent, e.g., hexane, heptane, and a tertiary alcohol, e.g., t-butanol, t-amyl alcohol. When methanol is used as the alcohol, the reaction can be promoted by adding an ether solvent such as t-butyl methyl ether or THF, or a tertiary alcohol such as t-butanol or t-amyl alcohol.

The pressure of carbon monoxide used herein is preferably ordinary to 15 MPa, more preferably 0.5~3 MPa. High quality of carbon monoxide is preferably used, but the mixed gas with hydrogen or an inert gas may be used if the mixed gas does not give bad effect to the reaction.

The reaction temperature is not limited and preferably 0~140° C., more preferably 15~50° C.

In this reaction, when an optically active epoxide as a reactant is used, an optically active β-hydroxyester is obtained without decrease of the optical purity. Epichlorohydrin is especially preferably used.

The present reaction, for example reaction of propylene oxide and methanol is shown by the following reaction scheme.

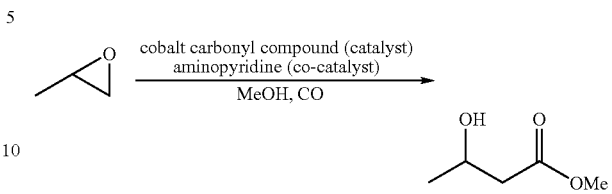

The reaction product of this reaction, a β-hydroxyester is easily purified by distillation under reduced pressure.

Catalyst in the solvent, cobalt is extracted in an aqueous layer as an aqueous basic cobalt salt by adding to the distilled residue a mineral acid such as hydrochloric acid, sulfuric acid or nitric acid and a nonaqueous organic solvent in accordance to known method. By adding sodium hydroxide or sodium carbonate to this aqueous layer, cobalt hydroxide or cobalt carbonate is recovered, respectively. These cobalt compounds can be reused.

EXAMPLE

The present invention is explained by Examples and Comparative examples, but the present invention should not be limited to these examples.

Example 1

(S)-4-Chloro-3-hydroxybutanoic acid ethyl ester

In a 50 mL-volumetric autoclave was added deaerated ethanol (10 mL), and thereto were added 4-aminopyridine (47 mg, 0.5 mmol) and (S)-epichlorohydrin (1.9 g, 20 mmol, >99% ee). Then to the mixture was added crystalline dicobaltoctacarbonyl complex (171 mg, 0.5 mmol). After covering the autoclave with a cap, carbon monoxide (1 MPa) was introduced therein and the mixture was reacted at 30° C. for 30 hours. After cooling to room temperature, the solvent was removed in vacuo. The residue was subjected to Kugelrohr distillation to give 4-chloro-3-hydroxybutanoic acid ethyl ester (3.1 g, 92%, >99% ee) as a colorless oil. bp: 80° C./0.6 mmHg.

Example 2

(S)-4-Chloro-3-hydroxybutanoic acid methyl ester

In a 50 mL-volumetric autoclave was added deaerated methanol (10 mL), and thereto were added 4-aminopyridine (47 mg, 0.5 mmol) and (S)-epichlorohydrin (1.9 g, 20 mmol, >99% ee). Then to the mixture was added crystalline dicobaltoctacarbonyl complex (171 mg, 0.5 mmol). After covering the autoclave with a cap, carbon monoxide (1 MPa) was introduced therein and the mixture was reacted at 33° C. for 25 hours. After cooling to room temperature, the solvent was removed in vacuo. The residue was subjected to Kugelrohr distillation to give (S)-4-chloro-3-hydroxybutanoic acid methyl ester (2.6 g, 85%, >99% ee) as a colorless oil.

Example 3

(R)-4-Chloro-3-hydroxybutanoic acid ethyl ester

In a 50 mL-volumetric autoclave were added deaerated ethanol (10 mL) and THF (10 mL), and thereto were added 4-dimethylaminopyridine (61 mg, 0.5 mmol) and (R)-epichlorohydrin (1.9 g, 20 mmol, >99% ee). Then to the mixture was added crystalline dicobaltoctacarbonyl complex (171 mg, 0.5 mmol). After covering the autoclave with a cap, carbon monoxide (2 MPa) was introduced therein and the mixture was reacted at 40° C. for 16 hours. After cooling to room temperature, the solvent was removed in vacuo. The residue was subjected to Kugelrohr distillation to give (R)-4-chloro-3-hydroxybutanoic acid ethyl ester (2.8 g, 83%, >99% ee) as a colorless oil.

Example 4

(S)-4-Ethoxy-3-hydroxybutanoic acid ethyl ester

In a 50 mL-volumetric autoclave were added deaerated ethanol (10 mL) and toluene, and thereto were added 4-aminopyridine (47 mg, 0.5 mmol) and (S)-ethylglycidyl ether (2.0 g, 20 mmol, >99% ee). Then to the mixture was added crystalline dicobaltoctacarbonyl complex (171 mg, 0.5 mmol). After covering the autoclave with a cap, carbon monoxide (1 MPa) was introduced therein and the mixture was reacted at 40° C. for 18 hours. After cooling to room temperature, the solvent was removed in vacuo. The residue was subjected to Kugelrohr distillation to give (S)-4-ethoxy-3-hydroxybutanoic acid ethyl ester (3.0 g, 85%, >99% ee) as a colorless oil.

Example 5

(R)-4-Ethoxy-3-hydroxybutanoic acid n-butyl ester

In a 50 mL-volumetric autoclave were added deaerated n-butanol (20 mL), and thereto were added 4-aminopyridine (47 mg, 0.5 mmol) and (R)-ethylglycidyl ether (2.0 g, 20 mmol, >99% ee). Then to the mixture was added crystalline dicobaltoctacarbonyl complex (171 mg, 0.5 mmol). After covering the autoclave with a cap, carbon monoxide (1 MPa) was introduced therein and the mixture was reacted at 45° C. for 12 hours. After cooling to room temperature, the solvent was removed in vacuo. The residue was subjected to Kugelrohr distillation to give (R)-4-ethoxy-3-hydroxybutanoic acid n-butyl ester (3.7 g, 90%, >99% ee) as a colorless oil.

Example 6

(S)-3-Hydroxyheptanoic acid ethyl ester

In a 50 mL-volumetric autoclave were added deaerated ethanol (10 mL) and ethyl acetate (10 mL), and thereto were added 4-aminopyridine (47 mg, 0.5 mmol) and (S)-1,2-epoxyhexane (2.0 g, 20 mmol, >99% ee). Then to the mixture was added crystalline dicobaltoctacarbonyl complex (171 mg, 0.5 mmol). After covering the autoclave with a cap, carbon monoxide (1 MPa) and hydrogen gas (1 MPa) were introduced therein and the mixture was reacted at 35° C. for 28 hours. After cooling to room temperature, the solvent was removed in vacuo. The residue was subjected to Kugelrohr distillation to give (S)-3-hydroxyheptanoic acid ethyl ester (2.92 g, 85%, >99% ee) as a colorless oil.

Example 7

(S)-4-Chloro-3-hydroxybutanoic acid isopropyl ester

In a 50 mL-volumeric autoclave were added deaerated isopropanol (20 mL), 4-aminopyridine 47 mg (0.5 mmol) and (S)-epichlorohydrin (1.9 g, 20 mmol, >99% ee). Then to the mixture was added crystalline dicobaltoctacarbonyl complex (171 mg, 0.5 mmol). After covering the autoclave with a cap, carbon monoxide (1.5 MPa) was introduced therein and the mixture was reacted at 40° C. for 25 hours. After cooling to room temperature, the solvent was removed in vacuo. The residue was subjected to Kugelrohr distillation to give (S)-4-chloro-3-hydroxybutanoic acid isopropyl ester (2.7 g, 80%, >99% ee) as a colorless oil.

Example 8

(S)-3-Hydroxybutanoic acid ethyl ester

In a 50 mL-volumeric autoclave were added deaerated ethanol (25 mL), 4-aminopyridine (47 mg, 0.5 mmol) and (S)-propyleneoxide (1.2 g, 20 mmol, >99% ee). Then to the mixture was added crystalline dicobaltoctacarbonyl complex (171 mg, 0.5 mmol). After covering the autoclave with a cap, carbon monoxide (1 MPa) and hydrogen gas (1 MPa) were introduced therein and the mixture was reacted at 40° C. for 24 hours. After cooling to room temperature, the solvent was removed in vacuo. The residue was subjected to Kugelrohr distillation to give 3-hydroxybutanoic acid ethyl ester (2.4 g, 92%, >99% ee) as a colorless oil.

Example 9

(S)-4-Phenoxy-3-hydroxybutanoic acid methyl ester

In a 50 mL-volumeric autoclave were added deaerated methanol (20 mL), 4-aminopyridine (47 mg, 0.5 mmol) and (S)-phenylglycidyl ether (3.0 g, 20 mmol, >99% ee). Then to the mixture was added crystalline dicobaltoctacarbonyl complex (171 mg, 0.5 mmol). After covering the autoclave with a cap, carbon monoxide (0.5 MPa) was introduced therein and the mixture was reacted at 30° C. for 30 hours. After cooling to room temperature, the solvent was removed in vacuo. The residue was subjected to Kugelrohr distillation to give (S)-4-phenoxy-3-hydroxybutanoic acid methyl ester (3.8 g, 90%, >99% ee) as a colorless oil.

Example 10

(R)-4-Benzyloxy-3-hydroxybutanoic acid methyl ester

In a 50 mL-volumetric autoclave were added deaerated methanol (15 mL) and THF (10 mL), and thereto were added 4-aminopyridine (47 mg, 0.5 mmol) and (R)-benzylglycidyl ether (3.3 g, 20 mmol, >99% ee). Then to the mixture was added crystalline dicobaltoctacarbonyl complex (171 mg, 0.5 mmol). After covering the autoclave with a cap, carbon monoxide (1 MPa) was introduced therein and the mixture was reacted at 35° C. for 24 hours. After cooling to room temperature, the solvent was removed in vacuo. The residue was subjected to Kugelrohr distillation to give (R)-4-benzyloxy-3-hydroxybutanoic acid methyl ester (4.0 g, 89%, >99% ee) as a colorless oil.

Example 11

(S)-4-Methoxy-3-hydroxybutanoic acid ethyl ester

In a 50 mL-volumetric autoclave were added deaerated ethanol (10 mL) and toluene (10 mL), and thereto were added 4-aminopyridine (47 mg, 0.5 mmol) and (S)-methylglycidyl ether (1.8 g, 20 mmol, >99% ee). Then to the mixture was added crystalline dicobaltoctacarbonyl complex (171 mg, 0.5 mmol). After covering the autoclave with a cap, carbon monoxide (1 MPa) was introduced therein and the mixture was reacted at 40° C. for 20 hours. After cooling to room temperature, the solvent was removed in vacuo. The residue was subjected to Kugelrohr distillation to give (S)-4-methoxy-3-hydroxybutanoic acid ethyl ester (3.0 g, 92%, >99% ee) as a colorless oil.

Example 12

(S)-4-Chloro-3-hydroxybutanoic acid ethyl ester

In a 50 mL-volumetric autoclave were added deaerated ethanol (10 mL), and thereto were added cobalt acetate tetrahydrate (250 mg, 1 mmol) and 10% Pd/C (10 mg). After covering the autoclave with a cap, carbon monoxide (1 MPa) and hydrogen gas (1 MPa) were introduced therein, successively and the mixture was reacted at 80° C. for 3 hours. After 3 hours the mixture was cooled to room temperature, and the mixed gas was emitted to give a solution containing dicobaltoctacarbonyl complex. Thereto were added 4-aminopyridine (47 mg, 0.5 mmol) and (S)-epichlorohydrin (1.8 g, 20 mmol, >99% ee). After covering the autoclave with a cap, carbon monoxide (1 MPa) was introduced therein and the mixture was reacted at 35° C. for 28 hours. After temperature of the mixture was made room temperature, the solvent was removed in vacuo. The residue was subjected to Kugelrohr distillation to give (S)-4-chloro-3- hydroxybutanoic acid ethyl ester (3.1 g, 92%, >99% ee) as a colorless oil.

Example 13

(S)-3-Hydroxyheptanoic acid ethyl ester

After reduction of the catalyst in the same manner as in Example 12, thereto were added 4-aminopyridine (47 mg, 0.5 mmol) and (S)-epoxyhexane (2.0 g, 20 mmol, >99% ee), and carbon monoxide (1 MPa) was introduced therein. The mixture was reacted at 40° C. for 20 hours. After cooling to room temperature, the solvent was removed in vacuo. The residue was subjected to Kugelrohr distillation to give (S)-3-hydroxyheptanoic acid ethyl ester (2.92 g, 85%, >99% ee) as a colorless oil.

Example 14

(R)-4-Ethoxy-3-hydroxybutanoic acid ethyl ester

After reduction of the catalyst in the same manner as in Example 12, thereto were added 4-aminopyridine (47 mg, 0.5 mmol) and (R)-ethylglycidyl ether (2.0 g, 20 mmol, >99% ee). After covering the autoclave with a cap, carbon monoxide (2 MPa) was introduced therein and the mixture was reacted at 50° C. for 16 hours. After cooling to room temperature, the solvent was removed in vacuo. The residue was subjected to Kugelrohr distillation to give (R)-4-ethoxy-3-hydroxybutanoic acid ethyl ester (3.17 g, 90%, >99% ee) as a colorless oil.

Example 15

(S)-4-Chloro-3-hydroxybutanoic acid isopropyl ester

In a 50 mL-volumetric autoclave were added deaerated isopropanol (10 mL) and THF (10 mL), and thereto were added cobalt acetate tetrahydrate (250 mg, 1 mmol) and 10% Rh/C (10 mg). After covering the autoclave with a cap, carbon monoxide (1 MPa) and hydrogen gas (1 MPa) were introduced therein, successively and the mixture was reacted at 100° C. for 3 hours. After 3 hours the mixture was cooled to room temperature, and the mixed gas was emitted to give a solution containing dicobaltoctacarbonyl complex. Thereto were added 4-aminopyridine (47 mg, 0.5 mmol) and (S)-epichlorohydrin (1.8 g, 20 mmol, >99% ee). After covering the autoclave with a cap, carbon monoxide (1.3 MPa) was introduced therein and the mixture was reacted at 35° C. for 30 hours. After cooling to room temperature, the solvent was removed in vacuo. The residue was subjected to Kugelrohr distillation to give (S)-4-chloro-3-hydroxybutanoic acid isopropyl ester (3.3 g, 92%, >99% ee) as a colorless oil.

Example 16

(R)-4-Ethoxy-3-hydroxybutanoic acid methyl ester

In a 50 mL-volumetric autoclave were added deaerated methanol (10 mL) and toluene (10 mL), and thereto were added cobalt hydroxide (Co: 60%) (100 mg, 1 mmol) and 10% Pd/C (10 mg). After covering the autoclave with a cap, carbon monoxide (1 MPa) and hydrogen gas (1 MPa) were introduced therein, successively and the mixture was reacted at 120° C. for 2 hours. After 2 hours the mixture was cooled to room temperature, and the mixed gas was emitted to give a solution containing dicobaltoctacarbonyl complex. Thereto were added 4-aminopyridine (47 mg, 0.5 mmol) and (R)-ethylglycidyl ether (2.0 g, 20 mmol, >99% ee). After covering the autoclave with a cap, carbon monoxide (1 MPa) was introduced therein and the mixture was reacted at 40° C. for 20 hours. After cooling to room temperature, the solvent was removed in vacuo. The residue was subjected to Kugelrohr distillation to give (R)-4-ethoxy-3-hydroxybutanoic acid methyl ester (2.92 g, 90%, >99% ee) as a colorless oil.

Example 17

(S)-4-Chloro-3-hydroxybutanoic acid methyl ester

In a 50 mL-volumetric autoclave were added deaerated methanol (5 mL) and t-butanol (3 mL), and thereto were added 4-aminopyridine (47 mg, 0.5 mmol) and (S)-epichlorohydrin (1.9 g, 20 mmol, >99% ee). Then to the mixture was added crystalline dicobaltoctacarbonyl complex (171 mg, 0.5 mmol). After covering the autoclave with a cap, carbon monoxide (1 MPa) was introduced therein and the mixture was reacted at 40° C. for 5 hours. After cooling to room temperature, the solvent was removed in vacuo. The residue was subjected to Kugelrohr distillation to give (S)-4-chloro-3-hydroxybutanoic acid methyl ester (2.8 g, 92%, >99% ee) as a colorless oil.

Example 18

(R)-4-Benzyloxy-3-hydroxybutanoic acid methyl ester

In a 50 mL-volumetric autoclave were added deaerated methanol (10 mL) and t-butyl methyl ether (10 mL), and thereto were added 4-aminopyridine (47 mg, 0.5 mmol) and (R)-benzylglycidyl ether (3.3 g, 20 mmol, >99% ee). Then to the mixture was added crystalline dicobaltoctacarbonyl complex (171 mg, 0.5 mmol). After covering the autoclave with a cap, carbon monoxide (1 MPa) was introduced therein and the mixture was reacted at 40° C. for 6 hours. After cooling to room temperature, the solvent was removed in vacuo. The residue was subjected to Kugelrohr distillation to give (R)-4-benzyloxy-3-hydroxybutanoic acid methyl ester (4.3 g, 95%, >99% ee) as a colorless oil.

Example 19

(S)-4-Methoxy-3-hydroxybutanoic acid methyl ester

In a 50 mL-volumetric autoclave were added deaerated methanol (10 mL) and t-amyl alcohol (10 mL), and thereto were added 4-aminopyridine (47 mg, 0.5 mmol) and (S)-methylglycidyl ether (1.8 g, 20 mmol, >99% ee). Then to the mixture was added crystalline dicobaltoctacarbonyl complex (171 mg, 0.5 mmol). After covering the autoclave with a cap, carbon monoxide (1 MPa) was introduced therein and the mixture was reacted at 40° C. for 8 hours. After cooling to room temperature, the solvent was removed in vacuo. The residue was subjected to Kugelrohr distillation to give (S)-4-methoxy-3-hydroxybutanoic acid methyl ester (2.7 g, 92%, >99% ee) as a colorless oil.

Comparative Examples 1 to 4 and Example 1A

Using following co-catalysts instead of 4-aminopyridine, the reaction were conducted for 16 hours in the same manner and conditions as in Example 1 and the degrees of conversion were shown in Table 1. According to the results, when the co-catalyst used in the present invention was not used, the reaction did not proceed enough. The degree of conversion after 16 hours on Example 1 was shown as Example 1A, for reference.

TABLE 1

| | Co-catalyst | Degree of conversion |
|---|---|---|
| Comparative example 1 | 3-hydroxypyridine | 44% |
| Comparative example 2 | pyridine | 38% |
| Comparative example 3 | imidazole | 49% |
| comparative example 4 | potassium carbonate | 28% |
| Example 1A | 4-aminopyridine | 74% |

On the other hand, even the reaction is conducted for 16 hours in the absence of co-catalyst (4-aminopyridine) in the same manner and condition as in Example 1, 4-chloro-3-hydroxybutanoic acid ethyl ester was obtained only in 8% yield.

The invention claimed is:

1. A process for preparation of a β-hydroxyester which comprises reacting an epoxide, an alcohol and carbon monoxide in the presence of a cobalt carbonyl compound as catalyst, and as co-catalyst, a pyridine derivative having an amino substituent group represented by the following formula (1),

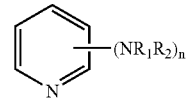

(1)

wherein $R_1$ and $R_2$ are independently hydrogen atom, formyl group, acyl group, alkoxycarbonyl group, substituted or unsubstituted alkyl group, substituted or unsubstituted aralkyl group, substituted or unsubstituted aryl group, or $R_1$ and $R_2$ may be taken together with the adjacent nitrogen atom to form a ring, and n is an integer of 1, the amino substituent group is at position 4 of the pyridine ring, and said pyridine ring is unsubstituted or substituted by C1 to 6 alkyl group or may be fused at its positions 2 and 3 with a benzene ring.

2. The process for preparation of a β-hydroxyester according to claim 1 wherein the pyridine derivative having an amino substituent group is one represented by the following formula (1a):

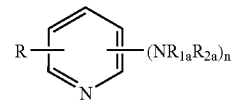

(1a)

wherein R is hydrogen atom or C1 to 6 alkyl group, $R_{1a}$ and $R_{2a}$ are independently, hydrogen atom, C1 to 10 alkyl group, or benzyl group, or $R_{1a}$ and $R_{2a}$ may be taken together with the adjacent nitrogen atom to form a 5 to 6 membered ring, and n is an integer of 1.

3. The process for preparation of a β-hydroxyester according to claim 1 wherein the pressure of carbon monoxide is 0.5 to 3 MPa.

4. The process for preparation of a β-hydroxyester according to claim 1 wherein the reaction is carried out at a range of 15 to 50° C.

5. The process for preparation of a β-hydroxyester according to claim 1 wherein the pyridine derivative having the amino substituent group is 4-aminopyridine or 4-dimethylaminopyridine.

6. The process for preparation of a β-hydroxyester according to claim 5 wherein the pyridine derivative having the amino substituent group is 4-aminopyridine.

7. The process for preparation of a β-hydroxyester according to claim 1 wherein the amount of the pyridine derivative is 0.3 to 1 mole equivalent to cobalt metal.

8. The process for preparation of a β-hydroxyester according to claim 1 wherein the cobalt carbonyl compound is dicobaltoctacarbonyl complex or a product containing dicobaltoctacarbonyl complex.

9. The process for preparation of a β-hydroxyester according to claim 1 wherein the epoxide is an 1,2-epoxide.

10. The process for preparation of a β-hydroxyester according to claim 9 wherein the 1,2-epoxide is optically active epichlorohydrin.

11. The process for preparation of a β-hydroxyester according to claim 1 wherein the alcohol is a primary or secondary alcohol having 10 carbon atoms or less.

12. The process for preparation of a β-hydroxyester according to claim 11 wherein the alcohol is an aliphatic alcohol having 6 carbon atoms or less.

13. The process for preparation of a β-hydroxyester according to claim 12 wherein an ether solvent or a tertiary alcohol is added when the alcohol is methanol.

* * * * *